(12) United States Patent
Han et al.

(10) Patent No.: US 7,501,422 B2
(45) Date of Patent: Mar. 10, 2009

(54) PROLINAMIDE-TETRAZOLE DERIVATIVES AS NK3 RECEPTOR ANTAGONISTS

(75) Inventors: Bo Han, Shanghai (CN); Henner Knust, Rheinfelden (DE); Matthias Nettekoven, Grenzach-Wyhlen (DE); Hasane Ratni, Habsheim (FR); Xihan Wu, Shanghai (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/129,720

(22) Filed: May 30, 2008

(65) Prior Publication Data
US 2008/0306089 A1    Dec. 11, 2008

(30) Foreign Application Priority Data
Jun. 7, 2007 (EP) ................... 07109783

(51) Int. Cl.
*A61K 31/496* (2006.01)
*C07D 403/04* (2006.01)

(52) U.S. Cl. .................. 514/254.05; 544/366
(58) Field of Classification Search ........... None
See application file for complete search history.

(56) References Cited

U.S. PATENT DOCUMENTS
2004/0034019 A1    2/2004    Tomlinson et al.

OTHER PUBLICATIONS

Tooney et al., Neurosci. Letters, vol. 283 pp. 185-188 (2000).
Giardina et al., Exp. Opin. Ther. Patents vol. 10, pp. 939-960 (2000).
Jung et al., Neuroscience vol. 74 pp. 403-414 (1996).
Marco et al., Neuropeptides vol. 32, pp. 481-488 (1998).
Kamali, F., Current Opinion in Investigational Drugs, vol. 2(7) pp. 950-956 (2001).
Albert et al. Expert Opinion on Therapeutic Patents, 16:7 (2006) 925-937.
Albert et at. J.Med. Chem. 45:18 (2002), 3972-3983.

*Primary Examiner*—Emily Bernhardt
(74) *Attorney, Agent, or Firm*—George W. Johnston; Patricia S. Rocha-Tramaloni; Kimberly J. Prior

(57) ABSTRACT

The present invention relates to a compound of formula I

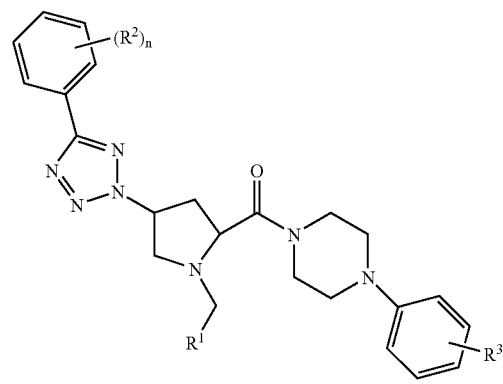

wherein
$R^1$, $R^2$, $R^3$, and n are as defined herein or to a pharmaceutically acceptable acid addition salt thereof. These compounds are NK3 receptor antagonists, useful for the treatment of such disorders as depression, pain, bipolar disorders, psychosis, Parkinson's disease, schizophrenia, anxiety, and attention deficit hyperactivity disorder (ADHD).

7 Claims, No Drawings

PROLINAMIDE-TETRAZOLE DERIVATIVES AS NK3 RECEPTOR ANTAGONISTS

PRIORITY TO RELATED APPLICATION(S)

This application claims the benefit of European Patent Application No. 07109783.6, filed Jun. 7, 2007, which is hereby incorporated by reference in its entirety.

BACKGROUND OF THE INVENTION

The three main mammalian tachykinins, substance P(SP), neurokinin A (NKA) and neurokinin B (NKB) belong to the family of neuropeptides sharing the common COOH-terminal pentapeptide sequence of Phe-X-Gly-Leu-Met-$NH_2$. As neurotransmitters, these peptides exert their biological activity via three distinct neurokinin (NK) receptors termed as NK-1, NK-2 and NK-3. SP binds preferentially to the NK-1 receptor, NKA to the NK-2 and NKB to the NK-3 receptor.

The NK-3 receptor is characterized by a predominant expression in CNS and its involvement in the modulation of the central monoaminergic system has been shown. These properties make the NK-3 receptor a potential target for central nervous system disorders such as anxiety, depression, bipolar disorders, Parkinson's disease, schizophrenia and pain (*Neurosci. Letters*, 2000, 283, 185-188; *Exp. Opin. Ther. Patents* 2000, 10, 939-960; *Neuroscience*, 1996, 74, 403-414; *Neuropeptides*, 1998, 32, 481-488).

Schizophrenia is one of the major neuropsychiatric disorders, characterized by severe and chronic mental impairment. This devastating disease affects about 1% of the world's population. Symptoms begin in early adulthood and are followed by a period of interpersonal and social dysfunction. Schizophrenia manifests as auditory and visual hallucinations, paranoia, delusions (positive symptoms), blunted affect, depression, anhedonia, poverty of speech, memory and attention deficits as well as social withdrawal (negative symptoms).

For decades scientists and clinicians have made efforts with the aim of discovering an ideal agent for the pharmacological treatment of schizophrenia. However, the complexity of the disorders, due to a wide array of symptoms, has hampered those efforts. There are no specific focal characteristics for the diagnosis of schizophrenia and no single symptom is consistently present in all patients. Consequently, the diagnosis of schizophrenia as a single disorder or as a variety of different disorders has been discussed but not yet resolved. The major difficulty in the development of a new drug for schizophrenia is the lack of knowledge about the cause and nature of this disease. Some neurochemical hypotheses have been proposed on the basis of pharmacological studies to rationalize the development of a corresponding therapy: the dopamine, the serotonin and the glutamate hypotheses. But taking into account the complexity of schizophrenia, an appropriate multireceptor affinity profile might be required for efficacy against positive and negative signs and symptoms. Furthermore, an ideal drug against schizophrenia would preferably have a low dosage allowing once-per-day dosage, due to the low adherence of schizophrenic patients.

In recent years clinical studies with selective NK1 and NK2 receptor antagonists appeared in the literature showing results for the treatment of emesis, depression, anxiety, pain and migraine (NK1) and asthma (NK2 and NK1). The most exciting data were produced in the treatment of chemotherapy-induced emesis, nausea and depression with NK1 and in asthma with NK2-receptor antagonists. In contrast, no clinical data on NK3 receptor antagonists have appeared in the literature until 2000. Osanetant (SR 142,801) from Sanofi-Synthelabo was the first identified potent and selective non-peptide antagonist described for the NK3 tachykinin receptor for the potential treatment of schizophrenia, which was reported in the literature (*Current Opinion in Investigational Drugs*, 2001, 2(7), 950-956 and *Psychiatric Disorders Study* 4, *Schizophrenia*, June 2003, Decision Resources, Inc., Waltham, Mass.). The proposed drug SR 142,801 has been shown in a phase II trial as active on positive symptoms of schizophrenia, such as altered behavior, delusion, hallucinations, extreme emotions, excited motor activity and incoherent speech, but inactive in the treatment of negative symptoms, which are depression, anhedonia, social isolation or memory and attention deficits.

The neurokinin-3 receptor antagonists have been described as useful in pain or inflammation, as well as in schizophrenia, *Exp. Opinion. Ther. Patents* (2000), 10(6), 939-960 and *Current Opinion in Investigational Drugs*, 2001, 2(7), 950-956 956 and *Psychiatric Disorders Study* 4, *Schizophrenia*, June 2003, Decision Recources, Inc., Waltham, Mass.).

SUMMARY OF THE INVENTION

The present invention provides a compound of formula I

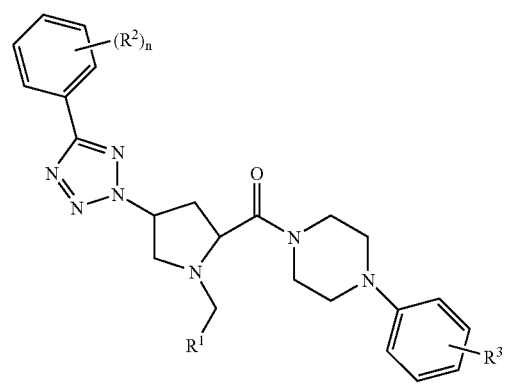

wherein $R^1$ is cycloalkyl or is phenyl unsubstituted or substituted by one or two halogen atoms;

$R^2$ is hydrogen or halogen;

$R^3$ is hydrogen, CN, lower alkoxy, lower alkyl or halogen;

n is 0, 1 or 2;

or a pharmaceutically acceptable acid addition salt thereof.

The invention includes all sterioisomeric forms, including individual diastereoisomers and enantiomers of the compound of formula (I) as well as racemic and non-racemic mixtures thereof.

The invention also provides pharmaceutical compositions which comprise a therapeutically effective amount of a compound of formula I and a pharmaceutically acceptable carrier. The invention further provides methods for the manufacture of the compounds and compositions of the invention.

The present compounds are high potential NK-3 receptor antagonists for the treatment of depression, pain, bipolar disorders, psychosis, Parkinson's disease, schizophrenia, anxiety and attention deficit hyperactivity disorder (ADHD).

The preferred indications are depression, psychosis, Parkinson's disease, schizophrenia, anxiety, and attention hyperactivity disorder (AHDH).

DETAILED DESCRIPTION OF THE INVENTION

The following definitions of the general terms used in the present description apply irrespective of whether the terms in question appear alone or in combination.

As used herein, the term "lower alkyl" denotes a straight- or branched-chain hydrocarbyl group containing from 1-7 carbon atoms, for example, methyl, ethyl, propyl, isopropyl, n-butyl, i-butyl, t-butyl and the like. Preferred lower alkyl groups are groups with 1-4 carbon atoms.

As used herein, the term "lower alkoxy" denotes a straight- or branched-chain alkyl group containing from 1-7 carbon atoms as described above and wherein the alkyl group is bonded via an oxygen atom.

The term "halogen" denotes chlorine, iodine, fluorine and bromine.

The term "cycloalkyl" denotes a saturated carbon ring containing from 3-7 carbon atoms, for example, cyclopropyl, cyclobutyl, cyclpentyl, cyclohexyl, cycloheptyl, and the like.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

Compounds of formula I, wherein $R^1$ is phenyl unsubstituted or substituted by one or two halogen atoms are preferred, for example the following compounds:

2-(4-{(2S,4S)-1-benzyl-4-[5-(2,4-difluoro-phenyl)-tetrazol-2-yl]-pyrrolidine-2-carbonyl}-piperazin-1-yl)-benzonitrile, 2-{4-[(2S,4S)-4-[5-(2,4-difluoro-phenyl)-tetrazol-2-yl]-1-(2-fluoro-benzyl)-pyrrolidine-2-carbonyl]-piperazin-1-yl}-benzonitrile, 2-{4-[(2S,4S)-4-[5-(2,4-difluoro-phenyl)-tetrazol-2-yl]-1-(3-fluoro-benzyl)-pyrrolidine-2-carbonyl]-piperazin-1-yl}-benzonitrile, 2-{4-[(2S,4S)-4-[5-(2,4-difluoro-phenyl)-tetrazol-2-yl]-1-(4-fluoro-benzyl)-pyrrolidine-2-carbonyl]-piperazin-1-yl}-benzonitrile, 2-(4-{(2S,4S)-1-(2-chloro-benzyl)-4-[5-(2,4-difluoro-phenyl)-tetrazol-2-yl]-pyrrolidine-2-carbonyl}-piperazin-1-yl)-benzonitrile, 2-(4-{(2S,4S)-1-(3-chloro-benzyl)-4-[5-(2,4-difluoro-phenyl)-tetrazol-2-yl]-pyrrolidine-2-carbonyl}-piperazin-1-yl)-benzonitrile, 2-(4-{(2S,4S)-1-(4-chloro-benzyl)-4-[5-(2,4-difluoro-phenyl)-tetrazol-2-yl]-pyrrolidine-2-carbonyl}-piperazin-1-yl)-benzonitrile and 2-(4-{(2S,4S)-1-(3,4-difluoro-benzyl)-4-[5-(2,4-difluoro-phenyl)-tetrazol-2-yl]-pyrrolidine-2-carbonyl}-piperazin-1-yl)-benzonitrile.

Compounds of formula I, wherein $R^1$ is cycloalkyl are also preferred, for example the following compound 2-(4-{(2S,4S)-1-cyclohexylmethyl-4-[5-(2,4-difluoro-phenyl)-tetrazol-2-yl]-pyrrolidine-2-carbonyl}-piperazin-1-yl)-benzonitrile.

The preparation of compounds of formula I of the present invention can be carried out in sequential or convergent synthetic routes. Syntheses of the compounds of the invention are shown in the following schemes. The skills required for carrying out the reaction and purification of the resulting products are known to those skilled in the art. The substituents and indices used in the following description of the processes have the significance given herein before unless indicated to the contrary.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by methods, known in the art, for example by the process described below, which process comprises reacting a compound of formula

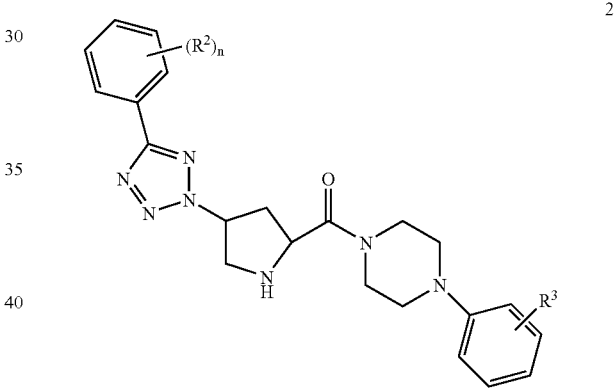

2 with $R^1C(O)H$, acetic acid and $NaBH(OAc)_3$ to give a compound of formula

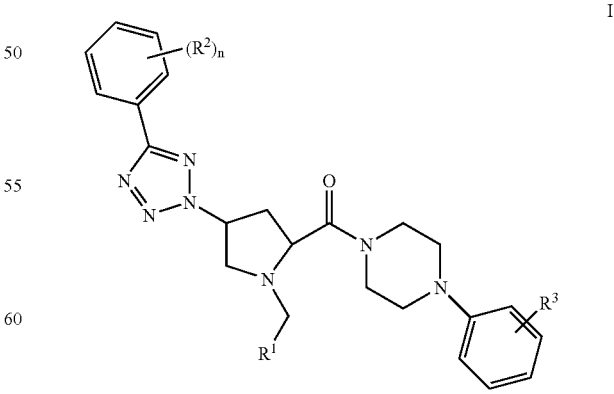

I wherein the substituents are as described above, and, if desired, converting a compound of formula I into a pharmaceutically acceptable salt.

The preparation of compounds of formula I is further described in more detail in scheme 1 and in examples 1-9.

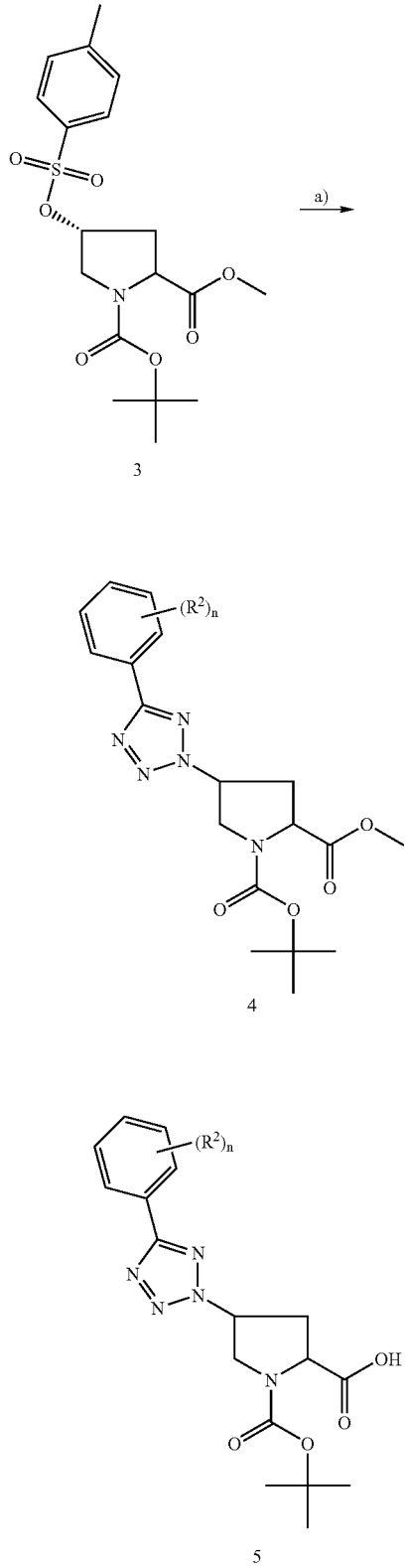

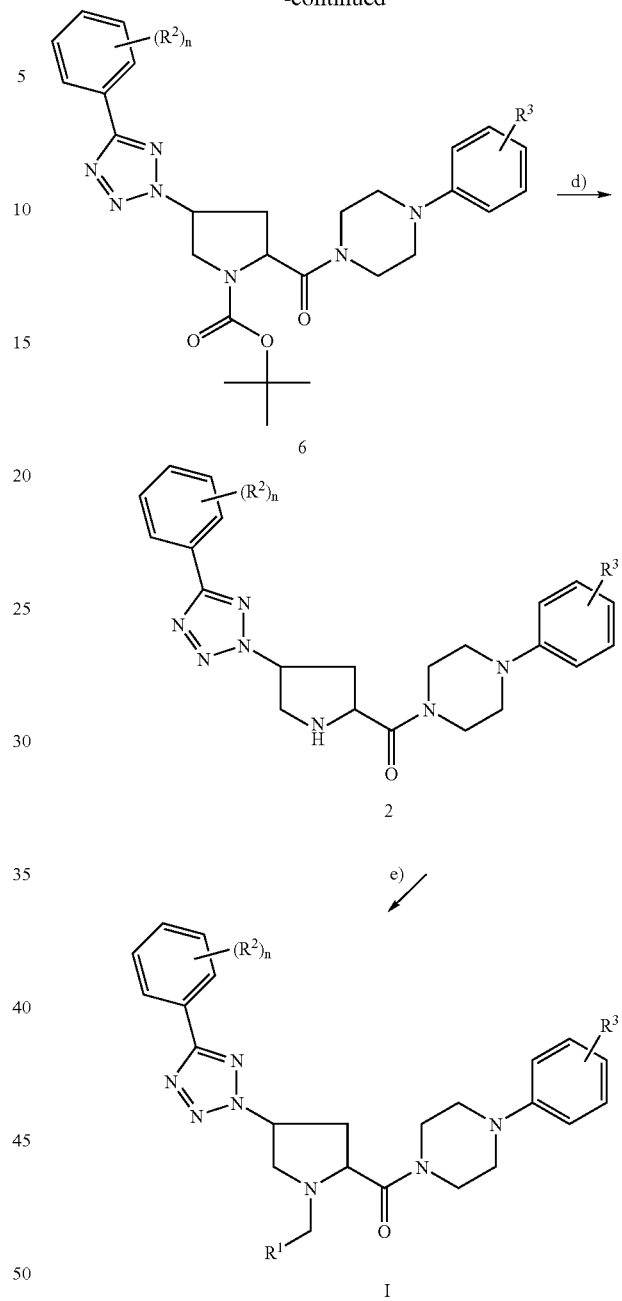

a) To a solution of a corresponding phenyl-tetrazole in DMF is added 2-[4-(2-cyano-phenyl)-piperazine-1-carbonyl]-4-(toluene-4-sulfonyloxy)-pyrrolidine-1-carboxylic acid tert-butyl ester and anhydrous sodium carbonate. The mixture is stirred at about 60 degree overnight. The solution is diluted with EA, washed, dried and concentrated to give the corresponding 4-[5-(phenyl)-tetrazol-2-yl]-pyrrolidine-1,2-dicarboxylic acid 1-tert-butyl ester 2-methyl ester (4).

b) To a solution of 4-[5-(phenyl)-tetrazol-2-yl]-pyrrolidine-1,2-dicarboxylic acid 1-tert-butyl ester 2-methyl ester (4) in MeOH cooled to 0 degree is LiOH, and the mixture is stirred overnight. After removal of MeOH, the residue is acidified with HCl, extracted with EA, dried and concentrated to give the corresponding 4-[5-(phenyl)-tetrazol-2-yl]-pyrrolidine-1,2-dicarboxylic acid 1-tert-butyl ester (5).

c) To a solution of 4-[5-(phenyl)-tetrazol-2-yl]-pyrrolidine-1,2-dicarboxylic acid 1-tert-butyl ester(5), HOBt, EDC.HCl and Et$_3$N in DCM is added a substituted phenyl-piperazin, for example 1-(2-cyanophenyl)-piperazine. The mixture is stirred overnight, and then washed with Na$_2$CO$_3$, brine, dried and concentrated to give 2-[4-(2-cyano-phenyl)-piperazine-1-carbonyl]-4-[5-(phenyl)-tetrazol-2-yl]-pyrrolidine-1-carboxylic acid tert-butyl ester (6).

d) 2-[4-(2-Cyano-phenyl)-piperazine-1-carbonyl]-4-[5-(phenyl)-tetrazol-2-yl]-pyrrolidine-1-carboxylic acid tert-butyl ester (6) is added to CF$_3$COOH, and the reaction mixture is stirred for about 5 h. After removal of CF$_3$COOH, the residue is dissolved in DCM, washed, dried and concentrated to give 2-(4-{4-[5-(phenyl)-tetrazol-2-yl]-pyrrolidine-2-carbonyl}-piperazin-1-yl)-benzonitrile (2).

e) 2-(4-{4-[5-(Phenyl)-tetrazol-2-yl]-pyrrolidine-2-carbonyl}-piperazin-1-yl)-benzonitrile (2), benzaldehyde and acetic acid (cat) is dissolved in DCM and the solution is stirred for 20 min. Then NaBH(OAc)$_3$ is added. The resulting mixture is warmed to r.t and stirred overnight. The solution is then washed with sat NaHCO$_3$, brine, dried and concentrated to afford 2-(4-{1-Benzyl-4-[5-(phenyl)-tetrazol-2-yl]-pyrrolidine-2-carbonyl}-piperazin-1-yl)-benzonitrile (I).

The salt formation is effected at room temperature in accordance with methods which are known per se and which are familiar to any person skilled in the art. Not only salts with inorganic acids, but also salts with organic acids come into consideration. Hydrochlorides, hydrobromides, sulphates, nitrates, citrates, acetates, maleates, succinates, methan-sulphonates, p-toluenesulphonates and the like are examples of such salts.

Abbreviations

DCM=dichloromethane;

DMF=N,N-dimethylformamide;

MS=mass spectroscopy;

EA=ethylacetate

EDC=1-(3-dimethylaminopropyl)-3-ethylcarbodiimide

HOBt=1-hydroxybenzotriazole hydrate

As mentioned earlier, the compounds of formula I and their pharmaceutically usable addition salts possess valuable pharmacological properties. It has been found that the compounds of the present invention are antagonists of neurokinin 3 (NK-3) receptors. The compounds were investigated in accordance with the tests given hereinafter.

Test Description:

The compounds were investigated in accordance with the tests given hereinafter.

[$^3$H]SR142801 Competition Binding Assay hNK3 receptor binding experiment were performed using [$^3$H]SR142801 (Catalog No. TRK1035, specific activity: 74.0 Ci/mmol, Amersham, G E Healthcare UK limited, Buckinghamshire, UK) and membrane isolated from HEK293 cells transiently expressing recombinant human NK3 receptor. After thawing, the membrane homogenates were centrifuged at 48,000×g for 10 min at 4° C., the pellets were resuspended in the 50 mM Tris-HCl, 4 mM MnCl$_2$, 1 µM phosphoramidon, 0.1% BSA binding buffer at pH 7.4 to a final assay concentration of 5 µg protein/well. For inhibition experiments, membranes were incubated with [$^3$H] SR142801 at a concentration equal to K$_D$ value of radioligand and 10 concentrations of the inhibitory compound (0.0003-10 µM) (in a total reaction volume of 500 µl) for 75 min at room temperature (RT). At the end of the incubation, membranes were filtered onto unitfilter (96-well white microplate with bonded GF/C filter preincubated 1 h in 0.3% PEI+0.3% BSA, Packard BioScience, Meriden, Conn.) with a Filtermate 196 harvester (Packard BioScience) and washed 4 times with ice-cold 50 mM Tris-HCl, pH 7.4 buffer. Nonspecific binding was measured in the presence of 10 µM SB222200 for both radioligands. The radioactivity on the filter was counted (5 min) on a Packard Top-count microplate scintillation counter with quenching correction after addition of 45 µl of microscint 40 (Can berra Packard S. A., Zürich, Switzerland) and shaking for 1 h. Inhibition curves were fitted according to the Hill equation: $y=100/(1+(x/IC_{50})^{nH})$, where $n_H$=slope factor using Excel-fit 4 software (Microsoft). IC$_{50}$ values were derived from the inhibition curve and the affinity constant (K$_i$) values were calculated using the Cheng-Prussoff equation $K_i=IC_{50}/(1+[L]/K_D)$ where [L] is the concentration of radioligand and K$_D$ is its dissociation constant at the receptor, derived from the saturation isotherm. All experiments were performed in duplicate and the mean±standard error (SEM) of the individual K$_i$ values was calculated.

The results of compounds 1-9 with a hNK-3 receptor affinity were shown in the following table 1.

TABLE 1

| Example | Data K$_i$ (µM) |
|---------|-----------------|
| 1 | 0.084 |
| 2 | 0.023 |
| 3 | 0.320 |
| 4 | 0.965 |
| 5 | 0.280 |
| 6 | 0.295 |
| 7 | 0.208 |
| 8 | 0.696 |
| 9 | 0.387 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semi-solid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatin capsules, solutions, emulsions, or suspensions. The pharmaceutical compositions also can be administered rectally, for example, in the form of suppositories, or parenterally, for example, in the form of injection solutions.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The dosage at which compounds of the invention can be administered can vary within wide limits and will, of course, be fitted to the individual requirements in each particular case. In general, in the case of oral administration a daily dosage of about 10 to 1000 mg per person of a compound of general formula (I) should be appropriate, although the above upper limit can also be exceeded when necessary.

EXAMPLE A

Tablets of the following composition are manufactured in the usual manner:

|  | mg/tablet |
| --- | --- |
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
| --- | --- |
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatin capsules.

EXAMPLE C

Suppositories of the following composition are manufactured:

|  | mg/supp. |
| --- | --- |
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The following Examples illustrate the present invention without limiting it. All temperatures are given in degrees Celsius.

EXAMPLE 1

2-(4-{(2S,4S)-1-Benzyl-4-[5-(2,4-difluoro-phenyl)-tetrazol-2-yl]-pyrrolidine-2-carbonyl}-piperazin-1-yl)-benzonitrile a) (2S,4S)-4-[5-(2,4-Difluoro-phenyl)-tetrazol-2-yl]-pyrrolidine-1,2-dicarboxylic acid 1-tert-butyl ester 2-methyl ester To a solution of (2,4-difluoro-phenyl)-tetrazole (0.44 g, 1.1 mmol) in 5 ml DMF was added 0.1 g (0.55 mmol) of (2S,4R)-2-[4-(2-cyano-phenyl)-piperazine-1-carbonyl]-4-(toluene-4-sulfonyloxy)-pyrrolidine-1-carboxylic acid tert-butyl ester and anhydrous sodium carbonate (0.15 g, 1.4 mmol). The mixture was stirred vigorously at 60 degree overnight. The solution was diluted with 30 ml EA and washed with 1M $Na_2CO_3$, 5% citric acid and brine, dried and concentrated to give the crude product as yellow oil (0.14 g, 0.34 mmol). MS m/e=410.3 $[M+H]^+$.

b) (2S,4S)-4-[5-(2,4-Difluoro-phenyl)-tetrazol-2-yl]-pyrrolidine-1,2-dicarboxylic acid 1-tert-butyl ester To a solution of 4-[5-(2,4-difluoro-phenyl)-tetrazol-2-yl]-pyrrolidine-1,2-dicarboxylic acid 1-tert-butyl ester 2-methyl ester (0.14 g, 0.34 mmol) in MeOH (25 ml) cooled to 0 degree was added LiOH (0.06 g, 1.36 mmol), and the mixture was stirred overnight. After removal of MeOH, the residue was acidified with 2M HCl. The aqueous layer was extracted with EA, the organic solution was dried and concentrated to give title product as yellow oil (0.1 g, 0.25 mmol). MS m/e=396.3 $[M+H]^+$.

c) (2S,4S)-2-[4-(2-Cyano-phenyl)-piperazine-1-carbonyl]-4-[5-(2,4-difluoro-phenyl)-tetrazol-2-yl]-pyrrolidine-1-carboxylic acid tert-butyl ester To the solution of acid (0.1 g, 0.25 mmol), HOBt (0.051 g, 0.38 mmol), EDC.HCl (0.073 g, 0.38 mmol) and $Et_3N$ (0.07 ml, 0.5 mmol) in DCM (20 ml) was added 1-(2-cyanophenyl)-piperazine (0.056 g, 0.3 mmol). The mixture was stirred overnight, and then washed with saturated $Na_2CO_3$, brine, dried and concentrated to give title product as yellow oil (0.184 g, 0.33 mmol). MS m/e=565.3 [M+H]+.

d) (2S,4S)-2-(4-{4-[5-(2,4-Difluoro-phenyl)-tetrazol-2-yl]-pyrrolidine-2-carbonyl}-piperazin-1-yl)-benzonitrile 2-[4-(2-Cyano-phenyl)-piperazine-1-carbonyl]-4-[5-(2,4-difluoro-phenyl)-tetrazol-2-yl]-pyrrolidine-1-carboxylic acid tert-butyl ester (0.184 g, 0.33 mmol) was added to CF$_3$COOH (0.22 g, 1.95 mmol), and the reaction mixture was stirred for 5 h. After removal of CF$_3$COOH, the residue was dissolved in DCM, washed with sat. NaHCO$_3$, brine, dried and concentrated to give title product as yellow oil (0.136 g, 0.29 mmol). MS m/e=465.2 [M+H]+.

e) (2S,4S)-2-(4-{1-Benzyl-4-[5-(2,4-difluoro-phenyl)-tetrazol-2-yl]-pyrrolidine-2-carbonyl}-piperazin-1-yl)-benzonitrile 2-(4-{4-[5-(2,4-Difluoro-phenyl)-tetrazol-2-yl]-pyrrolidine-2-carbonyl}-piperazin-1-yl)-benzonitrile (0.136 g, 0.29 mmol), benzaldehyde (0.034 g, 0.32 mmol) and acetic acid (cat) was dissolved in DCM (20 ml) and the solution was stirred for 20 min. Then NaBH(OAc)$_3$ (0.12 g, 0.58 mmol) was carefully added. The resulting mixture was warmed to r.t and stirred overnight. The solution was then washed with sat NaHCO$_3$, brine, dried and concentrated to afford the title product as yellow oil (0.15 g, 6 mmol). MS m/e=555.4 [M+H]+.

EXAMPLE 2

2-{4-[(2S,4S)-4-[5-(2,4-Difluoro-phenyl)-tetrazol-2-yl]-1-(2-fluoro-benzyl)-pyrrolidine-2-carbonyl]-piperazin-1-yl}-benzonitrile As described for Example 1e, 2-(4-{4-[5-(2,4-difluoro-phenyl)-tetrazol-2-yl]-pyrrolidine-2-carbonyl}-piperazin-1-yl)-benzonitrile (60 mg, 0.13 mmol) was converted, using 2-fluoro-benzaldehyde (17 mg, 0.14 mmol) instead of benzaldehyde, to the title compound (6.1 mg, 8.2%) as light yellow oil. MS m/e=573.2 [M+H]+.

EXAMPLE 3

2-{4-[(2S,4S)-4-[5-(2,4-Difluoro-phenyl)-tetrazol-2-yl]-1-(3-fluoro-benzyl)-pyrrolidine-2-carbonyl]-piperazin-1-yl}-benzonitrile As described for Example 1e, 2-(4-{4-[5-(2,4-difluoro-phenyl)-tetrazol-2-yl]-pyrrolidine-2-carbonyl}-piperazin-1-yl)-benzonitrile (60 mg, 0.13 mmol) was converted, using 3-fluoro-benzaldehyde (17 mg, 0.14 mmol) instead of benzaldehyde, to the title compound (9.9 mg, 13.3%) as light yellow oil. MS m/e=573.1 [M+H]+.

EXAMPLE 4

2-{4-[(2S,4S)-4-[5-(2,4-Difluoro-phenyl)-tetrazol-2-yl]-1-(4-fluoro-benzyl)-pyrrolidine-2-carbonyl]-piperazin-1-yl}-benzonitrile As described for Example 1e, 2-(4-{4-[5-(2,4-difluoro-phenyl)-tetrazol-2-yl]-pyrrolidine-2-carbonyl}-piperazin-1-yl)-benzonitrile (60 mg, 0.13 mmol) was converted, using 4-fluoro-benzaldehyde (17 mg, 0.14 mmol) instead of benzaldehyde, to the title compound (8.2 mg, 11%) as light yellow oil. MS m/e=573.1 [M+H]+.

EXAMPLE 5

2-(4-{(2S,4S)-1-(2-Chloro-benzyl)-4-[5-(2,4-difluoro-phenyl)-tetrazol-2-yl]-pyrrolidine-2-carbonyl}-piperazin-1-yl)-benzonitrile As described for Example 1e, 2-(4-{4-[5-(2,4-difluoro-phenyl)-tetrazol-2-yl]-pyrrolidine-2-carbonyl}-piperazin-1-yl)-benzonitrile (60 mg, 0.13 mmol) was converted, using 2-chloro-benzaldehyde (20 mg, 0.14 mmol) instead of benzaldehyde, to the title compound (11 mg, 14.4%) as light yellow oil. MS m/e=589.1 (75%); 591.1 (25%) [M+H]+.

EXAMPLE 6

2-(4-{(2S,4S)-1-(3-Chloro-benzyl)-4-[5-(2,4-difluoro-phenyl)-tetrazol-2-yl]-pyrrolidine-2-carbonyl}-piperazin-1-yl)-benzonitrile As described for Example 1e, 2-(4-{4-[5-(2,4-difluoro-phenyl)-tetrazol-2-yl]-pyrrolidine-2-carbonyl}-piperazin-1-yl)-benzonitrile (60 mg, 0.13 mmol) was converted, using 3-chloro-benzaldehyde (20 mg, 0.14 mmol) instead of benzaldehyde, to the title compound (7.7 mg, 10%) as light yellow oil. MS m/e=589.1 (75%); 591.1 (25%) [M+H]+.

EXAMPLE 7

2-(4-{(2S,4S)-1-(4-Chloro-benzyl)-4-[5-(2,4-difluoro-phenyl)-tetrazol-2-yl]-pyrrolidine-2-carbonyl}-piperazin-1-yl)-benzonitrile As described for Example 1e, 2-(4-{4-[5-(2,4-difluoro-phenyl)-tetrazol-2-yl]-pyrrolidine-2-carbonyl}-piperazin-1-yl)-benzonitrile (60 mg, 0.13 mmol) was converted, using 4-chloro-benzaldehyde (20 mg, 0.14 mmol) instead of benzaldehyde, to the title compound (8.3 mg, 11%) as light yellow oil. MS m/e=589.1 (75%); 591.1 (25%) [M+H]+.

EXAMPLE 8

2-(4-{(2S,4S)-1-Cyclohexylmethyl-4-[5-(2,4-difluoro-phenyl)-tetrazol-2-yl]-pyrrolidine-2-carbonyl}-piperazin-1-yl)-benzonitrile As described for Example 1e, 2-(4-{4-[5-(2,4-difluoro-phenyl)-tetrazol-2-yl]-pyrrolidine-2-carbonyl}-piperazin-1-yl)-benzonitrile (60 mg, 0.13 mmol) was converted, using cyclohexanecarbaldehyde (16 mg, 0.14 mmol) instead of benzaldehyde, to the title compound (8.5 mg, 11.7%) as light yellow oil. MS m/e=561.3 [M+H]+.

EXAMPLE 9

2-(4-{(2S,4S)-1-(3,4-Difluoro-benzyl)-4-[5-(2,4-difluoro-phenyl)-tetrazol-2-yl]-pyrrolidine-2-carbonyl}-piperazin-1-yl)-benzonitrile As described for Example 1e, 2-(4-{4-[5-(2,4-difluoro-phenyl)-tetrazol-2-yl]-pyrrolidine-2-carbonyl}-piperazin-1-yl)-benzonitrile (60 mg, 0.13 mmol) was converted, using 3,4-difluoro-benzaldehyde (20 mg, 0.14 mmol) instead of benzaldehyde, to the title compound (10.4 mg, 13.5%) as light yellow oil. MS m/e=591.2 [M+H]+.

The invention claimed is:

1. A compound of formula I

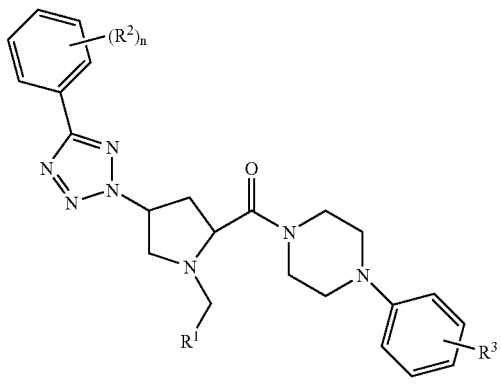

wherein
R¹ is cycloalkyl or is phenyl unsubstituted or substituted by one or two halogen atoms;
R² is hydrogen or halogen;
R³ is hydrogen, CN, lower alkoxy, lower alkyl or halogen; and
n is 0, 1 or 2;
or a pharmaceutically acceptable acid addition salt thereof.

2. A compound of claim 1, wherein R¹ is phenyl unsubstituted or substituted by one or two halogen atoms.

3. A compound of claim 2, selected from the group consisting of
2-(4-{(2S,4S)-1-benzyl-4-[5-(2,4-difluoro-phenyl)-tetrazol-2-yl]-pyrrolidine-2-carbonyl}-piperazin-1-yl)-benzonitrile,
2-{4-[(2S,4S)-4-[5-(2,4-difluoro-phenyl)-tetrazol-2-yl]-1-(2-fluoro-benzyl)-pyrrolidine-2-carbonyl]-piperazin-1-yl}-benzonitrile,
2-{4-[(2S,4S)-4-[5-(2,4-difluoro-phenyl)-tetrazol-2-yl]-1-(3-fluoro-benzyl)-pyrrolidine-2-carbonyl]-piperazin-1-yl}-benzonitrile,
2-{4-[(2S,4S)-4-[5-(2,4-difluoro-phenyl)-tetrazol-2-yl]-1-(4-fluoro-benzyl)-pyrrolidine-2-carbonyl]-piperazin-1-yl}-benzonitrile,
2-(4-{(2S,4S)-1-(2-chloro-benzyl)-4-[5-(2,4-difluoro-phenyl)-tetrazol-2-yl]-pyrrolidine-2-carbonyl}-piperazin-1-yl)-benzonitrile,
2-(4-{(2S,4S)-1-(3-chloro-benzyl)-4-[5-(2,4-difluoro-phenyl)-tetrazol-2-yl]-pyrrolidine-2-carbonyl}-piperazin-1-yl)-benzonitrile,
2-(4-{(2S,4S)-1-(4-chloro-benzyl)-4-[5-(2,4-difluoro-phenyl)-tetrazol-2-yl]-pyrrolidine-2-carbonyl}-piperazin-1-yl)-benzonitrile and
2-(4-{(2S,4S)-1-(3,4-difluoro-benzyl)-4-[5-(2,4-difluoro-phenyl)-tetrazol-2-yl]-pyrrolidine-2-carbonyl}-piperazin-1-yl)-benzonitrile.

4. A compound of claim 1, wherein R¹ is cycloalkyl.

5. A compound of claim 4, wherein the compound is
2-(4-{(2S,4S)-1-cyclohexylmethyl-4-[5-(2,4-difluoro-phenyl)-tetrazol-2-yl]-pyrrolidine-2-carbonyl}-piperazin-1-yl)-benzonitrile.

6. A pharmaceutical composition comprising a therapeutically effective amount of a compound of formula I

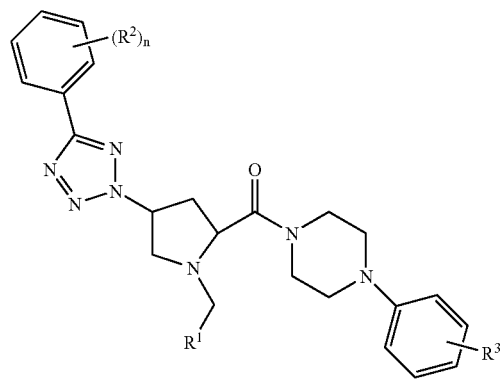

wherein
R¹ is cycloalkyl or is phenyl unsubstituted or substituted by one or two halogen atoms;
R² is hydrogen or halogen;
R³ is hydrogen, CN, lower alkoxy, lower alkyl or halogen; and
n is 0, 1 or 2;
or a pharmaceutically acceptable salt thereof and a pharmaceutically acceptable carrier.

7. A process for preparation of a compound of formula I,

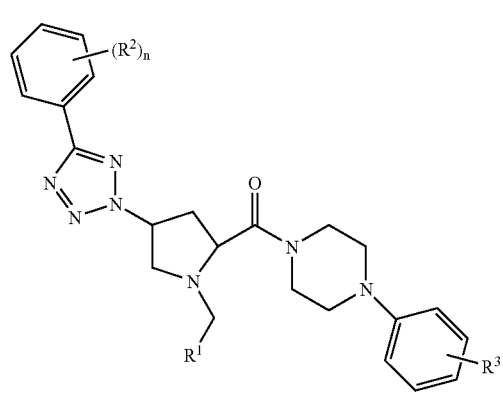

wherein
R¹ is cycloalkyl or is phenyl unsubstituted or substituted by one or two halogen atoms;
R² is hydrogen or halogen;
R³ is hydrogen, CN, lower alkoxy, lower alkyl or halogen; and
n is 0, 1 or 2;
which process comprises
reacting a compound of formula

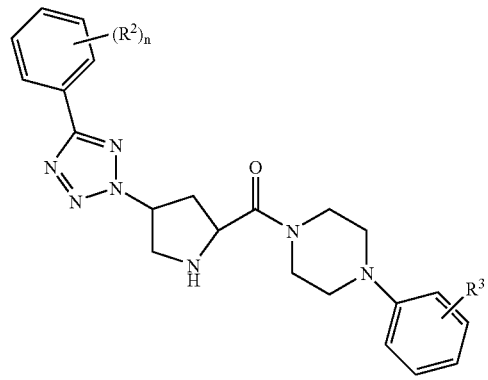
with R¹C(O)H, acetic acid and NaBH(OAc)$_3$
to give a compound of formula
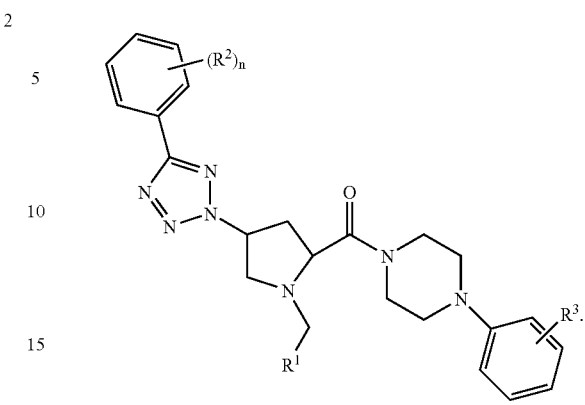
* * * * *